US012397286B2

(12) United States Patent
Yin et al.

(10) Patent No.: US 12,397,286 B2
(45) Date of Patent: Aug. 26, 2025

(54) PRECIOUS METAL-SUPPORTED EGGSHELL CATALYST AS WELL AS PREPARATION METHOD AND USE THEREOF

(71) Applicant: NINGBO INSTITUTE OF MATERIALS TECHNOLOGY & ENGINEERING, CHINESE ACADEMY OF SCIENCES, Ningbo (CN)

(72) Inventors: Hongfeng Yin, Ningbo (CN); Bin Li, Ningbo (CN); Bo Yan, Ningbo (CN); Jie Zhang, Ningbo (CN); Shenghu Zhou, Ningbo (CN)

(73) Assignee: NINGBO INSTITUTE OF MATERIALS TECHNOLOGY & ENGINEERING, CHINESE ACADEMY OF SCIENCES, Ningbo (CN)

( * ) Notice: Subject to any disclaimer, the term of this patent is extended or adjusted under 35 U.S.C. 154(b) by 627 days.

(21) Appl. No.: 17/595,938

(22) PCT Filed: Nov. 11, 2020

(86) PCT No.: PCT/CN2020/127943
§ 371 (c)(1),
(2) Date: Nov. 30, 2021

(87) PCT Pub. No.: WO2022/099488
PCT Pub. Date: May 19, 2022

(65) Prior Publication Data
US 2022/0347667 A1  Nov. 3, 2022

(51) Int. Cl.
| | | |
|---|---|---|
| B01J 35/30 | (2024.01) |
| B01J 21/04 | (2006.01) |
| B01J 21/06 | (2006.01) |
| B01J 21/08 | (2006.01) |
| B01J 21/12 | (2006.01) |
| B01J 23/02 | (2006.01) |
| B01J 23/46 | (2006.01) |
| B01J 23/58 | (2006.01) |
| B01J 23/63 | (2006.01) |
| B01J 23/656 | (2006.01) |
| B01J 23/89 | (2006.01) |
| B01J 29/00 | (2006.01) |
| B01J 29/46 | (2006.01) |

(Continued)

(52) U.S. Cl.
CPC .............. *B01J 35/397* (2024.01); *B01J 21/04* (2013.01); *B01J 21/063* (2013.01); *B01J 21/066* (2013.01); *B01J 21/08* (2013.01); *B01J 21/12* (2013.01); *B01J 23/02* (2013.01); *B01J 23/464* (2013.01); *B01J 23/58* (2013.01); *B01J 23/63* (2013.01); *B01J 23/6562* (2013.01); *B01J 23/8913* (2013.01); *B01J 23/892* (2013.01); *B01J 23/8926* (2013.01); *B01J 23/894* (2013.01); *B01J 23/8946* (2013.01); *B01J 29/00* (2013.01); *B01J 29/46* (2013.01); *B01J 29/76* (2013.01); *B01J 29/7615* (2013.01); *B01J 35/40* (2024.01); *B01J 37/0018* (2013.01); *B01J 37/0201* (2013.01); *B01J 37/0236* (2013.01); *B01J 37/088* (2013.01); *C07C 29/141* (2013.01); *C07C 29/154* (2013.01); *C07C 29/157* (2013.01); *C07C 29/158* (2013.01); *B01J 35/50* (2024.01); *B01J 35/55* (2024.01)

(58) Field of Classification Search
CPC ............ B01J 35/396–399; B01J 35/505; B01J 35/53; C07C 29/14–141
See application file for complete search history.

(56) References Cited

U.S. PATENT DOCUMENTS

| | | |
|---|---|---|
| 5,334,778 A | 8/1994 | Degussa |
| 6,342,646 B1 | 1/2002 | Du Pont |
| 2010/0137650 A1* | 6/2010 | Wolk ................... B01J 23/8993 585/270 |

FOREIGN PATENT DOCUMENTS

| | | |
|---|---|---|
| CN | 1178884 A | 4/1998 |
| CN | 1475472 A | 2/2004 |

(Continued)

OTHER PUBLICATIONS

Machine translation CN103769094, Sep. 23, 2015; pp. 1-35.*

(Continued)

*Primary Examiner* — Medhanit W Bahta
(74) *Attorney, Agent, or Firm* — Bayramoglu Law Offices LLC (57) ABSTRACT

A precious metal-supported eggshell catalyst with a preparation method and an application are provided. The precious metal-supported eggshell catalyst includes a carrier, a precious metal and a promoter. As an active component, the precious metal and the promoter are evenly distributed on surface of the carrier, wherein the promoter includes one or more than two of a precious metal, an alkaline earth metal, a transition metal lanthanide series metal, an actinium series metal and/or a metal oxide thereof. With a highly utilization of the precious metal, the precious metal-supported eggshell catalyst showed high conversion, good selectivity and excellent stability, and the precious metal-supported eggshell catalyst is used more than 300 hours with no obvious loss of activity in preparing 1,3-propanediol through hydrogenation of 3-hydroxypropionaldehyde aqueous solution. Furthermore, with large particles the precious metal-supported eggshell catalyst is easily separated from reaction products.

8 Claims, 1 Drawing Sheet

(51) Int. Cl.
*B01J 29/76* (2006.01)
*B01J 35/40* (2024.01)
*B01J 37/00* (2006.01)
*B01J 37/02* (2006.01)
*B01J 37/08* (2006.01)
*C07C 29/141* (2006.01)
*C07C 29/154* (2006.01)
*C07C 29/157* (2006.01)
*C07C 29/158* (2006.01)
*B01J 35/50* (2024.01)
*B01J 35/55* (2024.01)

(56) References Cited

FOREIGN PATENT DOCUMENTS

| CN | 1736604 A | 2/2006 |
| CN | 103769094 A | 5/2014 |
| CN | 105709778 A | 6/2016 |

OTHER PUBLICATIONS

Zhu, X. D. et al. "Deactivation of Ni/SiO2/Al2O3-catalyst in hydrogenation of 3-hydroxypropanal solution" Applied Catalysis A: General 155 (1997) 179-194 (Year: 1997).*

* cited by examiner

PRECIOUS METAL-SUPPORTED EGGSHELL CATALYST AS WELL AS PREPARATION METHOD AND USE THEREOF

CROSS REFERENCE TO RELATED APPLICATIONS

This application is the national stage entry of International Application No. PCT/CN2020/127943, filed on Nov. 11, 2020, the entire contents of which are incorporated herein by reference.

TECHNICAL FIELD

The present application relates to an eggshell catalyst, particularly to a precious metal-supported eggshell catalyst for preparing 1,3-propanediol through hydrogenation of 3-hydroxypropionaldehyde and a preparation method thereof, and use of the eggshell catalyst in preparation of 1,3-propanediol through hydrogenation of 3-hydroxypropionaldehyde, belonging to the technical field of catalyst preparation and application.

BACKGROUND 1,3-propanediol (1,3-PDO) is a widely used compound, which is a main raw material for producing poly (1,3-propanediol terephalate) fibers (PTT) except polyurethane and cyclic compounds. The prepared PTT fiber has both the performance of polyethylene terephthalate (PET) and good rebound resilience and pollution resistance of nylon, which can be widely applied to the fields of carpets, engineering plastics, garment fabrics and the like, and has become a hotspot on development of synthesized fibers in the world at present. Since the market demand of PTT fibers is gradually increased in recent years, it is estimated that the market scale of 1,3-PDO will be expanded from $490 million in 2019 to $871 million in 2024, with a compound annual rate of 12.2%, thus the development and application of the poly (1, 3-propanediol terephthalate) fiber has attracted extensive attentions again.

It is understood that, two routines for producing 1,3-PDO through heterogeneous catalysis are widely applied at present, including production of 1,3-PDO (Degussa-DuPont) from acraldehyde or production of 1, 3-PDO (Shell) from ethylene oxide respectively. In the two routines, an intermediate 3-hydroxypropionaldehyde (3-HPA) is produced through hydration of acraldehyde or hydroformylation of ethylene oxide, then 3-HPA is hydrogenated into 1,3-PDO. Therefore, development of high-performance solid hydrogenation catalyst has become an important subject for production of 1,3-PDO. There are three types of preferred hydrogenation catalysts for selectively hydrogenating 3-HPA into 1,3-PDO: (1) a Raney nickel catalyst or a Raney nickel catalyst modified by adding molybdenum, tungsten and the like; (2) a supported nickel catalyst (for example Ni/$Al_2O_3$), and (3) a supported platinum or palladium catalyst.

At present, many technical patents (CN1,178,8884, U.S. Pat. Nos. 6,342,646 and 5,334,778) involve two-step hydrogenation of 3-HPA into 1,3-PDO using precious metal supported catalysts in batch kettle reactors and continuous fixed bed reactors. Such the supported catalysts contain active components (for example ruthenium, platinum, palladium or their combinations) and supports (for example $TiO_2$, $Al_2O_3$, zeolite, MgO, $TiO_2$ or $SiO_2$). However, these catalysts usually show low activity and weak service life, resulting in using more precious metals to achieve relatively high conversion rate of 3-HPA, thereby causing relatively high catalyst cost. In order to more economically produce 1,3-PDO, it is very important to develop high-performance catalysts for 3-HPA hydrogenation.

In U.S. Pat. No. 6,342,646, a supported catalyst with a precious metal such as Ru as an active component is prepared, and the carrier is $TiO_2$ or $SiO_2$. The reaction for preparing 1,3-propanediol through hydrogenation of 3-hydroxypropionaldehyde is carried out in a fixed bed reactor. The hydrogen pressure of the reaction is 1-6 MPa, the reaction temperature is 30-180° C., the concentration of 3-hydroxypropionaldehyde solution is 5-15 wt %, the pH value of the 3-hydroxypropionaldehyde solution is 3.5-5.5, and the volume space velocity (LHSV) is 0.1-10 $h^{-1}$. After the reaction, the selectivity of 1,3-propanediol exceeds 98%. However, the content of the precious metal required by this catalyst is relatively high, which is about 2-5 wt %, and therefore its industrial cost is high.

SUMMARY

The main objective of the present application is to provide a precious metal-supported eggshell catalyst for preparation of 1,3-propanediol through hydrogenation of 3-hydroxypropionaldehyde and a preparation method thereof to overcome the defects in the prior art.

Another objective of the present application is to provide use of a precious metal-supported eggshell catalyst in preparation of 1,3-propanediol through hydrogenation of 3-hydroxypropionaldehyde.

To achieve the above objectives, the technical solution adopted by the present application is as follows:

The embodiments of the present application provide a precious metal-supported eggshell catalyst, the eggshell catalyst comprising a carrier, a precious metal supported on the carrier and serving as an active component and a promoter, wherein the precious metal and the promoter are evenly distributed on the surface of the carrier, and the promoter comprises a combination of any one or more than two of a precious metal, an alkaline earth metal, a transition metal lanthanide series metal and a actinium series metal and/or a metal oxide thereof.

In some preferred embodiments, the chemical formula of the eggshell catalyst is M-X/A in which A is the carrier, M is a precious metal element and X is a combination of any one or more than two of a precious metal element, an alkaline earth metal element, a transition metal lanthanide series metal element and an actinium series metal element.

In some preferred embodiments, the precious metal element comprises a combination of any one or more than two of Pt, Pd, Ir and Ru, but is not limited thereto.

In some preferred embodiments, the promoter comprises a combination of any one or more than two of Na, Ca, Ni, Co, Mn, Cu, La and Rh and/or a metal oxide thereof, but is not limited thereto.

The embodiments of the present application also provide a preparation method of a precious metal-supported eggshell catalyst as described above, comprising:

providing a metal salt precursor solution containing a precious metal element and a metal salt precursor solution containing an promoter metal element; and sufficiently impregnating the carrier into a mixed solution of the metal salt precursor solution containing the precious metal element and the metal salt precursor solution containing the promoter metal element, taking out the impregnated carrier, drying, and roasting, so as to obtain the precious metal-supported eggshell catalyst.

In some preferred embodiments, the impregnating comprises: the carrier is impregnated for 1-4 h in a mixed solution at 40-70° C., and then continues to be impregnated for 6-16 h at room temperature.

In some preferred embodiments, the roasting temperature is 400-500° C., the roasting time is 2-10 h.

The embodiments of the present application also provide use of a precious metal-supported eggshell catalyst as described above in preparation of 1,3-propanediol through hydrogenation of 3-hydroxypropionaldehyde.

Correspondingly, the embodiments of the present application also provide a preparation method of 1,3-propanediol, comprising:

carrying out reduction pretreatment on a precious metal-supported eggshell catalyst as described above; and     carrying out hydrogenation reaction on the eggshell catalyst subjected to reduction pretreatment and an aqueous solution containing 3-hydroxypropionaldehyde in a hydrogen atmosphere to obtain 1,3-propanediol.

Compared with the prior art, the present application at least has the beneficial effects:

1) The structure of the precious metal supported eggshell catalyst for preparing 1,3-propanediol through hydrogenation of 3-hydroxypropionaldehyde provided by the present application is innovated. The catalyst carrier is prepared into RASI ring particles, so that the catalyst structure is controlled as eggshell design. In this way, the main active component is evenly distributed on the surfaces of the carrier particles so that the utilization rate of the precious metal has been improved. On the one hand, the activity and service life of the catalyst are enhanced. On the other hand, the preparation cost of the catalyst is reduced, which is more conducive to the industrialization process for preparing 1,3-propanediol through hydrogenation of 3-hydroxypropionaldehyde;

2) In the precious metal supported eggshell catalyst for preparing 1,3-propanediol through hydrogenation of 3-hydroxypropionaldehyde provided by the present application, a second metal is introduced as the promoter, and an obvious synergistic effect occurs between the precious metal and the promoter metal on the surfaces of the catalyst carrier particles, thereby (1) promoting the hydrogenation conversion of 3-hydroxypropionaldehyde; (2) improving the selectivity of hydrogenation reaction of 3-hydroxypropionaldehyde and reducing side reactions; (3) realizing the high selectivity of 1,3-propanediol; (4) reducing the usage amount of the precious metal and the preparation cost of the catalyst;

3) The catalyst for preparing 1,3-propanediol through hydrogenation of 3-hydroxypropionaldehyde provided by the present application can be used for a continuous fixed bed hydrogenation process. When this catalyst is used for preparing 1,3-propanediol through hydrogenation of 3-hydroxypropionaldehyde, 300-hour continuous fixed bed hydrogenation test can be successfully realized; at the same time, after the used catalyst is calcined, this catalyst can still be used for preparing 1,3-propanediol through hydrogenation of 3-hydroxypropionaldehyde, and has good activity.

BRIEF DESCRIPTION OF THE DRAWINGS

For more clearly illustrating the embodiment of the present application or the technical solution in the prior art, drawings required to be used in the embodiments or in the prior art will be simply discussed below. Obviously, drawings in the following description are only some embodiments described in the present application. Other drawings will be made by persons of ordinary skill in the art according to these drawings without creative efforts.

DETAILED DESCRIPTION OF THE EMBODIMENTS

Figure 1:
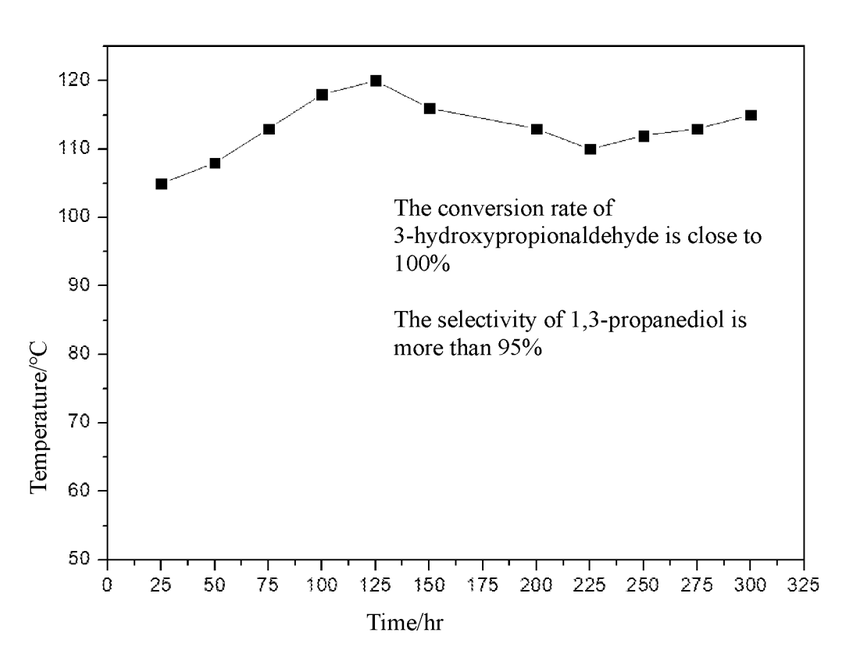
FIGURE is a schematic diagram of a 300-hour fixed bed continuous hydrogenation test result of a precious metal-supported eggshell catalyst in a typical embodiment of the present application.

As well known, the metal concentration distribution of a metal-supported catalyst is a key factor to affect hydrogenation reaction activity, selectivity and service life. Compared with the evenly distributed precious metal catalyst prepared through an equivalent-volume impregnation method, the structure of the catalyst is controlled as eggshell design, the active metal is evenly distributed on the surfaces of the particles so that the utilization rate of the precious metal is promoted. Meanwhile, a second metal is introduced as the promoter. Through the synergistic effect between the precious metal and the second metal, the catalytic effect on hydrogenation reaction is propelled, and therefore the catalyst of the disclosure exhibits more excellent activity, selectivity and service life on many hydrogenation reactions.

To overcome the poor activity, high catalyst cost and other defects of the existing hydrogenation catalyst in a fixed bend hydrogenation process for preparation of 1,3-propanediol from 3-hydroxypropionaldehyde, after long-term research and lots of practices, the inventor of this case put forward the technical solution of the present application. The present application mainly provides a new precious metal supported eggshell catalyst and a preparation method as well as its application in preparation of 1,3-propanediol from 3-hydroxypropionaldehyde. The catalyst provided by the present application exhibits the high conversion rate of reactant 3-hydroxypropionaldehyde, the high selectivity of product 1,3-propanediol and long service life in fixed bed hydrogenation. At the same time, the catalyst provided by the present application has high precious metal utilization rate and low preparation cost, can be repeatedly used through calcination after separation. Next, the technical solution as well as its implementation process and principle and the like will be further explained.

A precious metal-supported eggshell catalyst provided by one aspect of the embodiment of the present application comprises a carrier, a precious metal supported on the carrier and serving as an active component and a promoter, wherein the precious metal and the promoter are evenly distributed on the surface of the carrier, and the promoter comprises a combination of any one or more than two of a precious metal, an alkaline earth metal, a transition metal lanthanide series metal and a actinium series metal and/or a metal oxide thereof.

In some preferred embodiments, the chemical formula of the eggshell catalyst is M-X/A in which A is the carrier, M is a precious metal element and X is a combination of any one or more than two of the precious metal element, the alkaline earth metal element, the transition metal lanthanide series metal element and the actinium series metal element.

In some more preferred embodiments, the present application provides a catalyst for preparing 1,3-propanediol through hydrogenation of 3-hydroxypropionaldehyde. This catalyst is a precious metal-supported eggshell catalyst M-X/A in which the carrier A is a metal oxide or zeolite, the main activity component M is a precious metal, the promoter metal X is a second metal except the precious metal. The eggshell structure refers to the precious metal M and the promoter metal X being simultaneously and evenly distributed on the surface area of the carrier. Where, the carrier is an RASI ring particle composed of metal oxides or zeolite.

The design mechanism of the present application is that in the precious metal-supported eggshell catalyst, the second metal is introduced as the promoter, and an obvious synergistic effect occurs between the precious metal and the promoter metal on the surfaces of the catalyst carrier particles, thereby (1) promoting the hydrogenation conversion of 3-hydroxypropionaldehyde; (2) improving the selectivity of hydrogenation reaction of 3-hydroxypropionaldehyde and reducing side reactions; (3) realizing the high selectivity of 1,3-propanediol; and (4) reducing the usage amount of the precious metal and the preparation cost of the catalyst.

In some preferred embodiments, the main active component precious metal in the catalyst comprises a combination of any one or more than two of Pt, Pd, Ir and Ru, but is not limited to thereto.

In some preferred embodiments, the promoter is the second metal except the precious metal, or the precious metal. Where, the promoter can be any alkaline earth metals, transition metal lanthanide elements or actinide elements, or the like.

Further, the promoter can be present in a form of metal or metal oxide. For example, the promoter specifically comprises a combination of any one or more than two of Na, Ca, Ni, Co, Mn, Cu, La and Rh and/or a metal oxide thereof, but is not limited thereto.

In some preferred embodiments, the support amount of the precious metal in the eggshell catalyst is 0.1-10 wt %.

In some preferred embodiments, the support amount of the promoter in the eggshell catalyst is 1-50 wt %, preferably 1-20 wt %.

In some preferred embodiments, in the eggshell catalyst, based on the total amount of the catalyst, calculated by metal elements, a mass ratio of the promoter to the precious metal is 2:1-500:1.

In some preferred embodiments, the carrier is an RASI ring-shaped particle, and the material of the carrier comprises an oxide and/or a molecular sieve, but is not limited thereto.

Further, the component of the catalyst carrier A can be an oxide, for example a combination of any one or more than two of $\gamma$-$Al_2O_3$, $SiO_2$, MgO, $TiO_2$, $ZrO_2$ and amorphous aluminum silicate, and preferably comprises a combination of any one or more than two of $\gamma$-$Al_2O_3$, $SiO_2$, $TiO_2$ and amorphous aluminum silicate, but is not limited thereto.

Further, the component of the catalyst carrier A can be the molecular sieve, for example a combination of any one or more than two of ZSM-5, an HP molecular sieve, MCM-49, MCM-22, SAPO-11, SAPO-34, mordenite, $\beta$ Zeolite, L zeolite, Y zeolite and ultra-stable Y zeolite (USY), and preferably comprises a combination of any one or more than two of ZSM-5, an HP molecular sieve, MCM-49, SAPO-11 and $\beta$ Zeolite, but is not limited thereto.

Further, the component of the catalyst carrier A can be the mixture of the oxide and the molecular sieve.

In some preferred embodiments, the particle size of the carrier is 1-8 mm, preferably 2-5 mm.

Another aspect of the embodiment of the present application also provides a preparation of a precious metal-supported eggshell catalyst as described above, comprising:

providing a metal salt precursor solution containing a precious metal element and a metal salt precursor solution containing an promoter metal element; and sufficiently impregnating the carrier into a mixed solution of the metal salt precursor solution containing the precious metal element and the metal salt precursor solution containing the promoter metal element, taking out the impregnated carrier, drying, and roasting, so as to obtain the precious metal-supported eggshell catalyst.

In some preferred embodiments, a precious metal-supported eggshell catalyst for preparing 1,3-propanediol through hydrogenation of 3-hydroxypropionaldehyde is prepared by using an equivalent-volume impregnation method, the method specifically comprising the following steps:

(1) measuring the water absorption amount of the carrier, based on gram of water per 100 g of carrier as a unit;

(2) weighing metal salts of precious metals such as Pt, Pd, Ir and Ru by weight to prepare a metal salt precursor solution containing a precious metal element;

(3) weighing metal salts of promoter metals such as Na, Ca, Ni, Co, Mn, Cu, La and Rh by weight to prepared a metal salt precursor solution containing a promoter metal element;

(4) evenly mixing the two salt precursor solutions, adding the obtained mixed precursor solution into the carrier, uniformly stirring, and sufficiently impregnating; and (5) roasting the dried catalyst in a muffle furnace, and then cooling to obtain the catalyst.

In some preferred embodiments, in step (2), the precursor salt contained in the metal salt precursor solution containing the precious metal element comprises nitrate and/or chloride salt containing the precious metal element.

Further, the concentration of the metal salt precursor solution containing the precious metal element is 0.1-1.0 mol/L.

In some preferred embodiments, in step (3), the precursor salt contained in the metal salt precursor solution containing the promoter metal element comprises nitrate and/or chloride salt containing the promoter precious metal element.

Further, the concentration of the metal salt precursor solution containing the promoter metal element is 1.0-10.0 mol/L.

In some preferred embodiments, in step (4), the impregnating comprises: the carrier is impregnated for 1-4 h in a mixed solution at 40-70° C., and then continues to be impregnated for 6-16 h at room temperature.

Further, the impregnating process is carried out in a water bath of 40-70° C. for 1-4 h; and then the impregnating continues to be carried out for 10-14 h in a tray.

In some preferred embodiments, in step (5), the roasting is carried out in an air atmosphere, the roasting temperature is 400-500° C., and the roasting time is 2-10 h.

Further, the preparation method comprises: the temperature of the air atmosphere is raised to 400-550° C. using a temperature rising rate of 0.5-3° C./min.

Further, the roasting adopts programmed heating, the temperature rising rate is 0.5-3° C./min, and then the roasting is carried out for 3-6 h in the air atmosphere at the temperature of 400-550° C.

In some preferred embodiments, the preparation method of the catalyst carrier A comprises:

evenly mixing particles containing various carrier components with an binding agent to obtain a mixture; and molding the mixture, then shearing to a selected size, drying, and then roasting, so as to obtain the carrier.

In some more specific embodiments, a conventional method can be used to prepare the catalyst carrier A, specifically comprising the following steps:
(a) adding any one of the carriers or their mixture into a blender mixer to be stirred;
(b) preparing a proper amount of binding agent, and dropwise adding the binding agent into the carrier;
(c) adding the uniformly mixed carrier into an extrusion machine, molding in a die, shearing to a proper size, and finally drying at room temperature; and
(d) roasting in the muffle furnace, and then cooling.

Further, in step (a), the mixing and stirring rate of the blender mixer is 20-80 rpm, and the mixing and stirring time is 1-4 h.

Further, in step (b), the binding agent comprises a combination of any one or more than two of dilute nitric acid, citric acid and silica sol, but is not limited thereto.

Further, in step (b), a mass ratio of the binding agent to the carrier is 0.5-6:100, that is, the addition amount of the binding agent is 0.5-6 wt % of the mass of the carrier.

Further, in step (c), the shearing size is 2-5 mm.

Further, the roasting is carried out in the air atmosphere, the roasting temperature is 700-900° C., and the roasting time is 2-10 h.

Further, the preparation method comprises: the temperature of the air atmosphere is raised to 700-900° C. at a temperature rising rate of 1-5° C./min.

Further, in step (d), the roasting adopts programmed heating, the temperature rising rate is 1-5° C./min, and then the roasting is carried out for 3-6 h in the air atmosphere at the temperature of 700-900° C.

Another aspect of the embodiment of the present application also provides use of a precious metal-supported eggshell catalyst as described above in preparation of 1,3-propanediol through hydrogenation of 3-hydroxypropionaldehyde.

Correspondingly, another aspect of the embodiment of the present application also provides a preparation method of 1,3-propanediol, comprising:
carrying out reduction pretreatment on the precious metal-supported eggshell catalyst as described above; and
carrying out hydrogenation reaction on the eggshell catalyst subjected to reduction pretreatment and an aqueous solution containing 3-hydroxypropionaldehyde in a hydrogen atmosphere to obtain 1,3-propanediol.

In some preferred embodiments, the process conditions of the reduction pretreatment are as follows: the hydrogen pressure is 1.0-4.0 Mpa, the hydrogen space velocity is 50-500 $h^{-1}$, the reduction temperature is 350-500° C., and the reduction time is 2-10 h.

Further, the precious metal-supported eggshell catalyst needs to be reduced in the hydrogen atmosphere prior to use, and the reduction conditions are as follows: the hydrogen pressure is 0.1-5.0 MPa, the hydrogen space velocity is 10-1000 $h^{-1}$, the reduction temperature is 200-500° C., and the reduction time is 1-20 h, preferably, the hydrogen pressure is 1.0-4.0 Mpa, the hydrogen space velocity is 50-500 $h^{-1}$, the reduction temperature is 350-500° C., and the reduction time is 2-10 h.

In some preferred embodiments, the process conditions of the hydrogenation reaction are as follows: the temperature of the hydrogenation reaction is 40-130° C., the pressure of the hydrogenation reaction is 3-10 MPa, the concentration of the aqueous solution containing 3-hydroxypropionaldehyde is 5-15 wt %, the space velocity of the aqueous solution containing 3-hydroxypropionaldehyde is 0.1-1.0 $h^{-1}$, and a molar ratio of hydrogen to 3-hydroxypropionaldehyde is 2:1-20:1.

When the eggshell catalyst provided by the present application is used for preparing 1,3-propanediol through hydrogenation of 3-hydroxypropionaldehyde aqueous solution, the conversion rate of reactant 3-hydroxypropionaldehyde is high, the obtained 1,3-propanediol has good selectivity, the precious metal is high in use rate, and the catalyst has good stability and long service life. Furthermore, the catalyst has large particles, is easily separated from the reaction products, and can be repeatedly used after calcination.

Next, the technical solution of the present application will be described below through specific embodiments and accompanying drawings. It should be understood that one or more method steps mentioned in the present application do not exclude the existence of other method steps before and after the combined steps, or other method steps can be inserted before these explicitly mentioned steps; it should also be understood that these examples are used only to illustrate the present application but not limit the scope of the present application. Moreover, unless otherwise specified, the number of each method step is only a convenient tool for identifying each method step, not to limit the arrangement order of each method step or the scope of the present application. The change or adjustment of its relative relationship shall also be regarded as the scope of the present application without substantial change in the technical content.

EXAMPLES 1-32

An eggshell catalyst for preparing 1,3-propanediol through hydrogenation of 3-hydroxypropionaldehyde was prepared by using an equivalent-volume impregnation method.

Preparation of catalyst carrier:
(a) 2000 g of any one of molecular sieve ZSM-5, Hβ, MCM-49, SAPO-11, β zeolite or oxide γ-$Al_2O_3$, $SiO_2$ and $TiO_2$ or amorphous aluminum silicate or their mixture was selected and stirred in a blending machine;
(b) a proper amount of binding agent was selected, and dropwise added into a carrier;
(c) the above substances were sufficiently and uniformly stirred, the resulting mixture was added into an extruder, molded via a RASI ring and sheared to a proper size, and finally an eggshell carrier was prepared;
(d) the carrier was dried at room temperature, and sufficiently roasted in a muffle furnace. After calcination, the carrier was cooled to room temperature, and placed for later use.

Where, in step (a), the mixing rate of the mixing machine was 20-80 rpm, and the mixing and stirring time was 1-4 h. In step (b), the binding agent was selected from diluted nitric acid, citric acid and silica sol. In step (b), the addition amount of the binding agent was 0.5-6 wt % of the mass of dry carrier powder. In step (c), the shearing size was 2-5 mm. In step (d), the roasting adopted programmed heating, the temperature rising rate was 1-5° C./min, and then roasting was carried out for 2-10 h, preferably 3-6 h, at the temperature of 700-900° C. in an air atmosphere.

An eggshell catalyst was prepared using an equivalent-volume impregnation method:
(a) the water absorption amount of the carrier was measured, based on gram of $H_2O$ per 100 g of carrier;

(b) salts of precious metals Pt, Pd, Ir or Ru were weighed by weight to prepare a precursor solution;

(c) metal salts of promoter metals such as Na, Ca, Ni, Co, Mn, Cu, La and Rh were weighed by weight to prepare a precursor solution;

(d) the above precursor solutions were added into a catalyst carrier in a certain metering ratio to uniformly stirred, and sufficiently impregnated;

(e) the dried catalyst was roasted in a muffle furnace, and then cooled.

Where, in step (b), the precious metal salt can be selected from nitrate, chlorate and the like, and the molar concentration of the precursor solution of the precious metal is 0.1-1.0 mol/L.

In step (c), the precursor salt can be selected from nitrate, chlorate and the like, and the molar concentration of the precursor solution of the promoter metal is 1.0-10.0 mol/L.

In step (d), the impregnation process is carried out in water bath of 40-70° C., and lasted for 1-4 h; then impregnation was further carried out for 6-16 h in a tray at room temperature.

In step (e), the roasting adopted temperature programming, the temperature rising rate was 0.5-3° C./min, and then the roasting was carried out for 2-10 h at the temperature of 400-550° C. in an air atmosphere.

Reduction pretreatment: after roasting and cooling, the catalyst was loaded into a fixed bed reactor with a hydrogen pressure of 1.0-4.0 Mpa, a hydrogen space velocity of 50-500 $h^{-1}$, a reduction temperature of 350-500° C. and reduction time of 2-10 h. After the reduction procedure was completed, the conditions required for reduction pretreatment were adjusted.

The compositions of the catalysts obtained in examples 1-32 are shown in Table 1; the preparation process conditions used in examples 1-32 are shown in Table 2; for the different catalysts obtained in Table 2, the catalyst evaluation conditions and results are shown in Table 3.

TABLE 1

Compositions of catalysts in examples 1-32

| Examples | Component M | Salts of component M | Amount of component/ wt. % | Promoter X | Salts of promoter X | Amount of promoter/ wt. % | Carrier |
|---|---|---|---|---|---|---|---|
| Example 1 | Ir | $IrCl_3$ | 0.3 | Ni | $Ni(NO_3)_2$ | 5.0 | $\gamma\text{-}Al_2O_3$ |
| Example 2 | Ru | $RuCl_3 \cdot 3H_2O$ | 0.4 | Ni | $Ni(NO_3)_2$ | 5.0 | $\gamma\text{-}Al_2O_3$ |
| Example 3 | Pt | $Pt(NO_3)_2$ | 0.2 | Ni | $Ni(NO_3)_2$ | 5.0 | $\gamma\text{-}Al_2O_3$ |
| Example 4 | Pd | $PdCl_2$ | 0.2 | Ni | $Ni(NO_3)_2$ | 5.0 | $\gamma\text{-}Al_2O_3$ |
| Example 5 | Pd | $PdCl_2$ | 0.2 | Na | NaCl | 5.0 | $\gamma\text{-}Al_2O_3$ |
| Example 6 | Pd | $PdCl_2$ | 0.2 | Ca | $CaCl_2$ | 5.0 | $\gamma\text{-}Al_2O_3$ |
| Example 7 | Pd | $PdCl_2$ | 0.2 | Mn | $Mn(NO_3)_2$ | 5.0 | $\gamma\text{-}Al_2O_3$ |
| Example 8 | Pd | $PdCl_2$ | 0.2 | Cu | $Cu(NO_3)_2$ | 5.0 | $\gamma\text{-}Al_2O_3$ |
| Example 9 | Pd | $PdCl_2$ | 0.2 | Co | $Co(NO_3)_2$ | 5.0 | $\gamma\text{-}Al_2O_3$ |
| Example 10 | Pd | $PdCl_2$ | 0.2 | La | $La(NO_3)_3 \cdot 6H_2O$ | 5.0 | $\gamma\text{-}Al_2O_3$ |
| Example 11 | Pd | $PdCl_2$ | 0.2 | Rh | $Rh(NO_3)_3 \cdot nH_2O$ | 5.0 | $\gamma\text{-}Al_2O_3$ |
| Example 12 | Pd | $PdCl_2$ | 0.1 | Ni | $Ni(NO_3)_2$ | 5.0 | $\gamma\text{-}Al_2O_3$ |
| Example 13 | Pd | $PdCl_2$ | 5.0 | Ni | $Ni(NO_3)_2$ | 5.0 | $\gamma\text{-}Al_2O_3$ |
| Example 14 | Pd | $PdCl_2$ | 10 | Ni | $Ni(NO_3)_2$ | 5.0 | $\gamma\text{-}Al_2O_3$ |
| Example 15 | Pd | $PdCl_2$ | 0.2 | Ni | $Ni(NO_3)_2$ | 1.0 | $\gamma\text{-}Al_2O_3$ |
| Example 16 | Pd | $PdCl_2$ | 0.2 | Ni | $Ni(NO_3)_2$ | 20.0 | $\gamma\text{-}Al_2O_3$ |
| Example 17 | Pd | $PdCl_2$ | 0.2 | Ni | $Ni(NO_3)_2$ | 50.0 | $\gamma\text{-}Al_2O_3$ |
| Example 18 | Pd + Pt | $PdCl_2$ + $Pt(NO_3)_2$ | 0.1 + 0.1 | Ni | $Ni(NO_3)_2$ | 5.0 | $\gamma\text{-}Al_2O_3$ |
| Example 19 | Pd + Ir | $PdCl_2$ + $IrCl_3$ | 0.08 + 0.12 | Ni | $Ni(NO_3)_2$ | 5.0 | $\gamma\text{-}Al_2O_3$ |
| Example 20 | Pd | $PdCl_2$ | 0.2 | Ni + Na | $Ni(NO_3)_2$ + NaCl | 2.5 + 2.5 | $\gamma\text{-}Al_2O_3$ |
| Example 21 | Pd | $PdCl_2$ | 0.2 | Ni + La | $Ni(NO_3)_2$ + $La(NO_3)_3 \cdot 6H_2O$ | 2.5 + 2.5 | $\gamma\text{-}Al_2O_3$ |
| Example 22 | Pd | $PdCl_2$ | 0.2 | Ni | $Ni(NO_3)_2$ | 5.0 | $SiO_2$ |
| Example 23 | Pd | $PdCl_2$ | 0.2 | Ni | $Ni(NO_3)_2$ | 5.0 | $TiO_2$ |
| Example 24 | Pd | $PdCl_2$ | 0.2 | Ni | $Ni(NO_3)_2$ | 5.0 | ZSM-5 |

TABLE 1-continued

Compositions of catalysts in examples 1-32

| Examples | Component M | Salts of component M | Amount of component/ wt. % | Promoter X | Salts of promoter X | Amount of promoter/ wt. % | Carrier |
|---|---|---|---|---|---|---|---|
| Example 25 | Pd | PdCl$_2$ | 0.2 | Ni | Ni(NO$_3$)$_2$ | 5.0 | Amorphous aluminum silicate |
| Example 26 | Pd | PdCl$_2$ | 0.2 | Ni | Ni(NO$_3$)$_2$ | 5.0 | ZrO$_2$ |
| Example 27 | Pd | PdCl$_2$ | 0.2 | Ni | Ni(NO$_3$)$_2$ | 5.0 | MgO |
| Example 28 | Pd | PdCl$_2$ | 0.2 | Ni | Ni(NO$_3$)$_2$ | 5.0 | Hβ molecular sieve |
| Example 29 | Pd | PdCl$_2$ | 0.2 | Ni | Ni(NO$_3$)$_2$ | 5.0 | MCM-49 |
| Example 30 | Pd | PdCl$_2$ | 0.2 | Ni | Ni(NO$_3$)$_2$ | 5.0 | γ-Al$_2$O$_3$ + SiO$_2$ |
| Example 31 | Pd | PdCl$_2$ | 0.2 | Ni | Ni(NO$_3$)$_2$ | 5.0 | γ-Al$_2$O$_3$ + TiO$_2$ |
| Example 32 | Pd | PdCl$_2$ | 0.2 | Ni | Ni(NO$_3$)$_2$ | 5.0 | SiO$_2$ + TiO$_2$ |
| Comparative example A | Ir | IrCl$_3$ | 5 | Ni | Ni(NO$_3$)$_2$ | 35.0 | γ-Al$_2$O$_3$ |
| Comparative example B | Ru | RuCl$_3$ • 3H$_2$O | 7 | Ni | Ni(NO$_3$)$_2$ | 33.0 | γ-Al$_2$O$_3$ |
| Comparative example C | Pt | Pt(NO$_3$)$_2$ | 9 | Ni | Ni(NO$_3$)$_2$ | 31.0 | γ-Al$_2$O$_3$ |
| Comparative example D | Pd | PdCl$_2$ | 8 | Ni | Ni(NO$_3$)$_2$ | 32.0 | γ-Al$_2$O$_3$ |
| Comparative example E | Pd | PdCl$_2$ | 0.2 | Ni | Ni(NO$_3$)$_2$ | 0 | γ-Al$_2$O$_3$ |
| Comparative example F | Pd | PdCl$_2$ | 1.0 | Ni | Ni(NO$_3$)$_2$ | 0 | γ-Al$_2$O$_3$ |
| Comparative example G | Pd | PdCl$_2$ | 10.0 | Ni | Ni(NO$_3$)$_2$ | 0 | γ-Al$_2$O$_3$ |
| Comparative example H | Pd | PdCl$_2$ | 0 | Ni | Ni(NO$_3$)$_2$ | 5.0 | γ-Al$_2$O$_3$ |
| Comparative example I | Pd | PdCl$_2$ | 0 | Ni | Ni(NO$_3$)$_2$ | 25.0 | γ-Al$_2$O$_3$ |
| Comparative example J | Pd | PdCl$_2$ | 0.2 | Ni | Ni(NO$_3$)$_2$ | 5.0 | γ-Al$_2$O$_3$ |
| Comparative example K | Pd | PdCl$_2$ | 0.2 | Ni | Ni(NO$_3$)$_2$ | 5.0 | γ-Al$_2$O$_3$ |

TABLE 2

| Example | Water bath impregnation temperature/° C. | Impregnation time/h | Room temperature impregnation time/h | Roasting temperature/° C. | Roasting time/h | Reduction pressure/MPa | Reduction temperature/° C. | Reduction time/h | Reduction hydrogen space velocity/$h^{-1}$ |
|---|---|---|---|---|---|---|---|---|---|
| Example 1 | 65 | 2 | 10 | 550 | 4 | 1.0 | 500 | 6 | 300 |
| Example 2 | 50 | 2.5 | 10.5 | 450 | 3 | 1.2 | 350 | 5 | 500 |
| Example 3 | 70 | 1.5 | 11 | 400 | 3.5 | 2 | 400 | 8 | 350 |
| Example 4 | 60 | 3 | 12 | 500 | 4 | 1.5 | 450 | 4 | 200 |
| Example 5 | 40 | 3 | 12 | 500 | 4 | 1.5 | 500 | 4 | 200 |
| Example 6 | 70 | 3 | 12 | 500 | 4 | 1.5 | 400 | 4 | 200 |
| Example 7 | 40 | 3 | 12 | 500 | 4 | 1.5 | 500 | 4 | 200 |
| Example 8 | 40 | 3 | 12 | 500 | 4 | 1.5 | 500 | 4 | 200 |
| Example 9 | 40 | 3 | 12 | 500 | 4 | 1.5 | 500 | 4 | 200 |
| Example 10 | 60 | 3 | 12 | 500 | 4 | 1.5 | 550 | 4 | 200 |
| Example 11 | 60 | 3 | 12 | 500 | 4 | 1.5 | 450 | 10 | 200 |
| Example 12 | 40 | 1 | 6 | 400 | 2 | 0.1 | 200 | 1 | 10 |
| Example 13 | 40 | 3 | 11 | 400 | 2 | 0.1 | 350 | 1 | 30 |
| Example 14 | 40 | 4 | 16 | 400 | 2 | 0.1 | 500 | 1 | 50 |
| Example 15 | 70 | 1 | 6 | 550 | 10 | 5 | 200 | 20 | 250 |
| Example 16 | 70 | 3 | 11 | 550 | 10 | 5 | 350 | 20 | 500 |
| Example 17 | 70 | 4 | 16 | 550 | 10 | 5 | 500 | 20 | 1000 |
| Example 18 | 70 | 3 | 14 | 400 | 4 | 1.5 | 500 | 4 | 200 |
| Example 19 | 70 | 2 | 14 | 550 | 4 | 1.5 | 550 | 4 | 200 |
| Example 20 | 60 | 4 | 12 | 400 | 6 | 1.5 | 400 | 8 | 150 |
| Example 21 | 60 | 4 | 12 | 500 | 5 | 1.5 | 400 | 7 | 250 |
| Example 22 | 60 | 3 | 12 | 500 | 4 | 1.5 | 450 | 4 | 200 |
| Example 23 | 60 | 3 | 12 | 500 | 4 | 1.5 | 450 | 4 | 200 |
| Example 24 | 60 | 3 | 12 | 500 | 4 | 1.5 | 450 | 4 | 200 |
| Example 25 | 60 | 3 | 12 | 500 | 4 | 1.5 | 450 | 4 | 200 |
| Example 26 | 60 | 3 | 12 | 500 | 4 | 1.5 | 450 | 4 | 200 |
| Example 27 | 60 | 3 | 12 | 500 | 4 | 1.5 | 450 | 4 | 200 |
| Example 28 | 60 | 3 | 12 | 500 | 4 | 1.5 | 450 | 4 | 200 |
| Example 29 | 60 | 3 | 12 | 500 | 4 | 1.5 | 450 | 4 | 200 |
| Example 30 | 60 | 3 | 12 | 500 | 4 | 1.5 | 450 | 4 | 200 |
| Example 31 | 60 | 3 | 12 | 500 | 4 | 1.5 | 450 | 4 | 200 |
| Example 32 | 60 | 3 | 12 | 500 | 4 | 1.5 | 450 | 4 | 200 |
| Comparative example A | 65 | 2 | 10 | 550 | 4 | 1 | 500 | 6 | 300 |
| Comparative example B | 50 | 2.5 | 10.5 | 450 | 3 | 1.2 | 350 | 5 | 400 |
| Comparative example C | 70 | 1.5 | 11 | 400 | 3.5 | 2 | 400 | 8 | 350 |
| Comparative example D | 60 | 3 | 12 | 500 | 4 | 1.5 | 450 | 4 | 200 |
| Comparative example E | 60 | 3 | 12 | 500 | 4 | 1.5 | 450 | 4 | 200 |
| Comparative example F | 60 | 3 | 12 | 500 | 4 | 1.5 | 450 | 4 | 200 |
| Comparative example G | 60 | 3 | 12 | 500 | 4 | 1.5 | 450 | 4 | 200 |
| Comparative example H | 60 | 3 | 12 | 500 | 4 | 1.5 | 450 | 4 | 200 |

TABLE 2-continued

Preparation process conditions in examples 1-32

| Example | Water bath impregnation temperature/° C. | Impregnation time/h | Room temperature impregnation time/h | Roasting temperature/° C. | Roasting time/h | Reduction pressure/ MPa | Reduction temperature/° C. | Reduction time/h | Reduction hydrogen space velocity/$h^{-1}$ |
|---|---|---|---|---|---|---|---|---|---|
| Comparative example I | 60 | 3 | 12 | 500 | 4 | 1.5 | 450 | 4 | 200 |
| Comparative example J | 30 | 1 | 5 | 350 | 1 | 0.05 | 350 | 2 | 50 |
| Comparative example K | 80 | 4 | 20 | 600 | 1 | 0.05 | 500 | 10 | 500 |

Evaluation of Catalyst Activity

The newly prepared catalyst was loaded into a fixed bed reactor, and the reaction temperature in the hydrogenation section was 40-130° C.; the hydrogenation reaction pressure of hydrogenation section was 3-10 MPa; the concentration of 3-hydroxypropionaldehyde aqueous solution was 5-15 wt %; the space velocity of aqueous solution of 3-hydroxypropionaldehyde was 0.1-1.0 $h^{-1}$; the molar ratio of hydrogen to 3-hydroxypropionaldehyde was 2:1-20:1; sampling was carried out at the outlet section of the reactor for analysis, and the reaction conversion rate and selectivity were calculated. The reaction conditions and results of each example are shown in Table 3.

Conversion rate=(3-hydroxypropionaldehyde amount consumed by reaction per unit time)/(3-hydroxypropionaldehyde amount put into a reactor per unit time)

Selectivity=(generation amount of 1,3-propanediol per unit time)/(1,3-propanediol amount obtained after the reaction consumes raw materials per unit time)

TABLE 3

Evaluation conditions and results of catalysts in examples 1-31

| Example | Temperature/ ° C. | Reaction pressure/ MPa | $H_2$/3-hydroxypropionaldehyde | Space velocity/$h^{-1}$ | Conversion rate/% of 3-hydroxypropionaldehyde | Selectivity/ % of 1,3-propanediol |
|---|---|---|---|---|---|---|
| Example 1 | 65 | 5 | 4 | 0.4 | 100 | 89.5 |
| Example 2 | 85 | 5 | 4 | 0.6 | 100 | 93.6 |
| Example 3 | 85 | 4 | 4 | 0.6 | 100 | 92.4 |
| Example 4 | 108 | 4 | 4 | 0.6 | 100 | 100 |
| Example 5 | 108 | 10 | 4 | 0.6 | 97.6 | 98.2 |
| Example 6 | 135 | 6 | 4 | 0.6 | 96.5 | 99.1 |
| Example 7 | 132 | 5.5 | 4 | 0.6 | 99.5 | 96.1 |
| Example 8 | 125 | 5 | 4 | 0.6 | 99.2 | 97.1 |
| Example 9 | 139 | 5.5 | 4 | 0.6 | 99.6 | 98.4 |
| Example 10 | 82 | 4.5 | 4 | 0.6 | 100 | 95.2 |
| Example 11 | 84 | 5.5 | 4 | 0.6 | 100 | 96.1 |
| Example 12 | 40 | 4 | 4 | 0.6 | 100 | 99.5 |
| Example 13 | 130 | 4 | 4 | 0.6 | 99.9 | 98.7 |
| Example 14 | 108 | 3 | 4 | 0.6 | 100 | 98.5 |
| Example 15 | 108 | 4 | 20 | 0.6 | 98.5 | 96.2 |
| Example 16 | 108 | 6 | 4 | 0.6 | 95.4 | 98.1 |
| Example 17 | 108 | 6 | 4 | 0.6 | 97.8 | 96.7 |
| Example 18 | 98 | 5 | 4 | 0.6 | 96.8 | 95.6 |
| Example 19 | 95 | 5 | 4 | 0.6 | 97.6 | 97.8 |
| Example 20 | 108 | 6 | 4 | 0.6 | 91.6 | 95.2 |
| Example 21 | 108 | 6 | 4 | 0.6 | 92.1 | 96.8 |
| Example 22 | 108 | 4 | 2 | 0.6 | 100 | 93.5 |
| Example 23 | 108 | 4 | 4 | 1.0 | 100 | 92.6 |
| Example 24 | 108 | 4 | 4 | 1.0 | 100 | 94.6 |
| Example 25 | 108 | 4 | 4 | 1.0 | 100 | 94.1 |
| Example 26 | 108 | 4 | 4 | 1.0 | 100 | 93.8 |
| Example 27 | 108 | 4 | 4 | 1.0 | 100 | 92.9 |
| Example 28 | 108 | 4 | 4 | 1.0 | 100 | 92.7 |
| Example 29 | 108 | 4 | 4 | 1.0 | 100 | 93.3 |
| Example 30 | 108 | 4 | 4 | 0.1 | 100 | 94.2 |
| Example 31 | 108 | 4 | 4 | 0.6 | 100 | 93.1 |
| Example 32 | 108 | 4 | 4 | 0.6 | 100 | 93.9 |
| Comparative example A | 65 | 5 | 4 | 0.4 | 71.2 | 79.9 |
| Comparative example B | 85 | 5 | 4 | 0.6 | 70.1 | 78.4 |
| Comparative example C | 85 | 4 | 4 | 0.6 | 73.3 | 75.6 |

TABLE 3-continued

Evaluation conditions and results of catalysts in examples 1-31

| Example | Temperature/ °C. | Reaction pressure/ MPa | $H_2$/3-hydroxy-propion-aldehyde | Space velocity/$h^{-1}$ | Conversion rate/% of 3-hydroxypropion-aldehyde | Selectivity/% of 1,3-propanediol |
|---|---|---|---|---|---|---|
| Comparative example D | 108 | 4 | 4 | 0.6 | 74.6 | 71.1 |
| Comparative example E | 108 | 4 | 4 | 0.6 | 85.2 | 33.5 |
| Comparative example F | 108 | 4 | 4 | 0.6 | 86.6 | 80.5 |
| Comparative example G | 108 | 4 | 4 | 0.6 | 82.2 | 85.1 |
| Comparative example H | 108 | 4 | 4 | 0.6 | 75.2 | 82.3 |
| Comparative example I | 108 | 4 | 4 | 0.6 | 76.1 | 83.1 |
| Comparative example J | 108 | 4 | 4 | 0.6 | 45.8 | 62.9 |
| Comparative example K | 108 | 4 | 4 | 0.6 | 86.1 | 85.3 |

Example 33

The prepared hydrogenation catalyst in example 4 was loaded into a fixed bed reactor, and the reaction temperature in the hydrogenation section was 85° C.; the hydrogenation reaction pressure in the hydrogenation section was 4 MPa; the concentration of the reaction raw material 3-hydroxypropionaldehyde aqueous solution was 12 wt %; the aqueous solution space velocity of 3-hydroxypropionaldehyde is 0.6 $h^{-1}$; the molar ratio of hydrogen to 3-hydroxypropionaldehyde was 4:1. Through 300-hour fixed bed continuous hydrogenation reaction, samples were taken at the outlet section of the reactor for analysis, the reaction conversion rate and selectivity were calculated. The conversion rate of 3-hydroxypropionaldehyde was 99.9%, and the selectivity of 1,3-propanediol was 96% (see the FIGURE). This example shows that the catalyst of the present application has better stability and longer service life.

Example 34

The catalyst in example 33 after reaction was reduced and regenerated in a fixed bed reactor, the hydrogen pressure was 4.0 MPa, the hydrogen space velocity was 300 $h^{-1}$, the reduction temperature was 500° C., and the reduction time was 8 h. The reduced and regenerated catalyst was adjusted to the required reaction conditions. The reaction temperature of the hydrogenation section was 85° C.; the hydrogenation reaction pressure of the hydrogenation section was 4 MPa; the concentration of the 3-hydroxypropionaldehyde aqueous solution was 12 wt %; the aqueous solution space velocity of 3-hydroxypropionaldehyde is 0.6 $h^{-1}$; the molar ratio of hydrogen to 3-hydroxypropionaldehyde was 4:1. Samples were taken and analyzed at the outlet section of the reactor, and the reaction conversion rate and selectivity were calculated. The conversion rate of 3-hydroxypropionaldehyde was 98.9%, and the selectivity of 1,3-propanediol was 91%. This example shows that the catalyst of the present application can still be used after being reduced and regenerated.

Comparative Examples A-D

A non-eggshell catalyst is generally prepared by an excessive impregnation method. The preparation method was as follows:

The carrier powder was added into the mixer and stirred at 20-80 rpm for 1-4 h. The binding agent was added dropwise to the stirred carrier powder, and the mass fraction of the binder was preferably 1-6% of the mass of the carrier powder. Then the well-mixed carrier was added into the extruder, molded in a columnar mold, and sheared into 2-5 mm strips. In an air atmosphere of 90-150° C., the sheared carrier was subjected to standing and drying for 12-24 hours, and then calcined in a muffle furnace at 700-900° C. for 5-15 h.

Next, a large amount of precursor solutions of precious metals and promoter metals were prepared respectively. After the two precursor solutions were uniformly mixed, the pH of the precursor mixed solution was adjusted to 1-6 with an aqueous HCl solution. The obtained carrier was placed in the mixed solution and adsorbed at a water bath temperature of 40-70° C. for 12-24 h, so that the carrier can fully adsorb precious metals and promoter metals. After the adsorption process was completed, the metal solution on the surface of the carrier was washed with deionized water. Afterwards, the impregnated particles were subjected to standing for 12-24 h in an air atmosphere of 90-130° C., and then calcined in the muffle furnace at 450-650° C. for 5-10 h.

The compositions of catalysts in comparative examples A-D are shown in Table 1, the preparation conditions are shown in Table 2, and the catalysis evaluation conditions and results are shown in Table 3. By comparing the catalyst evaluation results of comparative examples A-D, it can be seen that the high conversion rate of 3-hydroxypropionaldehyde and the high selectivity of product 1,3-propanediol are obtained. Compared with the non-eggshell catalyst, the eggshell catalyst needs fewer precious metals and promoter metals, and has higher metal utilization rate and lower preparation cost.

Comparative Examples E-G

The compositions of catalysts in comparative examples E-G are shown in Table 1, the preparation conditions are shown in Table 2, and the catalysis evaluation conditions and results are shown in Table 3. By comparing the evaluation results of the catalysts in comparative examples E-F, it can be seen that for the catalyst that only supports the precious metal Pd and does not contain the promoter metal Ni, because there is no synergistic effect between the metal and the promoter metal, the conversion rate of 3-hydroxypropionaldehyde and the selectivity of product 1,3-propanediol are significantly reduced, further proving that the synergistic effect between the metal and the promoter metal has a promotion effect on this reaction. Meanwhile, by comparing the catalysis evaluation results of comparative example G and example 4, it can be seen that without the synergistic effect between the precious metal Pd and the promoter metal Ni, more precious metal support amount is needed to reach the same catalysis evaluation result as that in example 4, illustrating the synergistic effect between metals promotes the activity of the precious metal and greatly improves the usage rate of the precious metal, thereby reducing the preparation cost of the catalyst.

Comparative Examples H-I

The compositions of catalysts in comparative examples H-I are shown in Table 1, the preparation conditions are shown in Table 2, and the catalysis evaluation conditions and results are shown in Table 3. By comparing the evaluation results of the catalysts in examples H-I, it can be seen that the catalyst that only supports the promoter metal Ni and does not contain the precious metal Pd still has a certain conversion rate of 3-hydroxypropionaldehyde and selectivity of product 1,3-propanediol. However, because there is no synergistic effect between the precious metal and the promoter metal, its result shows a poorer effect than that of the catalyst simultaneously supporting the precious metal Pd and the promoter metal Ni. Meanwhile, compared with the results of comparative examples E-F, the precious metal Pd plays an important role in hydrogenation reaction of 3-hydroxypropionaldehyde.

Comparative Examples J-K

The compositions of catalysts in comparative examples J-K are shown in Table 1, the preparation conditions are shown in Table 2, and the catalysis evaluation conditions and results are shown in Table 3. By comparing the evaluation results of the catalysts of comparative examples J-K and example 4, it can be seen that the optimal preparation process conditions of the catalyst are as shown in the preparation process conditions of example 4.

In summary, the catalyst for preparing 1,3-propanediol through hydrogenation of 3-hydroxypropionaldehyde provided by the present application can be used for a continuous fixed-bed hydrogenation process. When the catalyst is used in a process for preparing 1,3-propanediol by hydrogenation of 3-hydroxypropionaldehyde, a continuous fixed-bed hydrogenation test of more than 300 hours can be successfully realized; meanwhile, after the used catalyst is calcined, this catalyst can still be used in the process for preparing 1,3-propanediol by hydrogenation of 3-hydroxypropionaldehyde, and has good activity.

The aspects, embodiments, features, and examples of the present application should be regarded as being illustrative in all aspects and are not intended to limit the present application. The scope of the present application is only defined by the claims. Without departing from the spirit and scope of the claimed application, those skilled in the art will understand other embodiments, modifications, and uses.

The use of titles and chapters in the present application is not meant to limit the present application; each chapter can be applied to any aspects, embodiments or features of the present application.

Throughout the present application, where a composition is described as having, containing, or including specific components, or where a process is described as having, containing, or including specific process steps, it is expected that the composition taught in the present application is also basically composed of or consists of the described components, and the process taught in the present application is basically composed of the described process steps or a set of described process steps.

It should be understood that the order of the steps or the order of performing specific actions is not very important, as long as the teachings of the present application remain operable. In addition, two or more steps or actions can be performed simultaneously.

In addition, the inventor of this case also referred to the foregoing embodiments and conducted experiments with other raw materials, process operations and process conditions described in this specification to obtain relatively ideal results.

Although the present application has been described with reference to illustrative embodiments, those skilled in the art will understand that various other changes, omissions and/or additions can be made without departing from the spirit and scope of the present application. Furthermore, substantive equivalents can be used to replace the elements in the embodiments. In addition, many modifications can be made to allow specific situations or materials to adapt to the teachings of the present application without departing from the scope of the present application. Therefore, this patent is intended to include all the embodiments included with the scope of the appended claims rather than limiting the present application to the specific embodiments for implementing the present application.

What is claimed is:

1. A method of using a precious metal-supported eggshell catalyst, wherein the precious metal-supported eggshell catalyst comprises a carrier, a precious metal supported on the carrier and serving as an active component, and a promoter,
    wherein the precious metal and the promoter are evenly distributed on a surface of the carrier, and the promoter comprises a combination of any one or more than two of a precious metal element, an alkaline earth metal element, a transition metal element, a lanthanide series metal element, and/or a metal oxide of the metal element, wherein the method comprises using the precious metal-supported eggshell catalyst in a preparation of 1,3-propanediol through a hydrogenation of 3-hydroxypropionaldehyde, and wherein the preparation of 1,3-propanediol comprises:
    carrying out a reduction pretreatment on the precious metal-supported eggshell catalyst;
    carrying out a hydrogenation reaction on the precious metal-supported eggshell catalyst subjected to a reduction pretreatment and an aqueous solution containing 3-hydroxypropionaldehyde in a hydrogen atmosphere to obtain the 1,3-propanediol;
    wherein process conditions of the reduction pretreatment are as follows: a hydrogen pressure is 0.1-5.0 MPa, a hydrogen space velocity is 10-1000 $h^{-1}$, a reduction temperature is 200-500° C., and a reduction time is 1-20 hours;
    wherein process conditions of the hydrogenation reaction are as follows: a temperature of the hydrogenation reaction is 40-130° C., a pressure of the hydrogenation reaction is 3-10 MPa, a concentration of the aqueous solution containing the 3-hydroxypropionaldehyde is 5-15 wt %, a space velocity of the aqueous solution containing the 3-hydroxypropionaldehyde is 0.1-1.0 $h^{-1}$, and a molar ratio of hydrogen to the 3-hydroxypropionaldehyde is 2:1-20:1.

2. A preparation method of 1,3-propanediol by using a precious metal-supported eggshell, wherein the precious metal-supported eggshell catalyst comprises a carrier, a precious metal supported on the carrier and serving as an active component, and a promoter, wherein the precious metal and the promoter are evenly distributed on a surface of the carrier, and the promoter comprises a combination of any one or more than two of a precious metal element, an alkaline earth metal element, a transition metal element, a lanthanide series metal element, and/or a metal oxide of the precious metal element, wherein the method comprises— carrying out a reduction pretreatment on the precious metal-supported eggshell catalyst;

carrying out a hydrogenation reaction on the precious metal-supported eggshell catalyst subjected to a reduction pretreatment and an aqueous solution containing 3-hydroxypropionaldehyde in a hydrogen atmosphere to obtain the 1,3-propanediol;

wherein process conditions of the reduction pretreatment are as follows: a hydrogen pressure is 0.1-5.0 MPa, a hydrogen space velocity is 10-1000 $^{-1}$, a reduction temperature is 200-500° C., and a reduction time is 1-20 hours;

wherein process conditions of the hydrogenation reaction are as follows: a temperature of the hydrogenation reaction is 40-130° C., a pressure of the hydrogenation reaction is 3-10 MPa, a concentration of the aqueous solution containing the 3-hydroxypropionaldehyde is 5-15 wt %, a space velocity of the aqueous solution containing the 3-hydroxypropionaldehyde is 0.1-1.0 $h^{-1}$ and a molar ratio of hydrogen to the 3-hydroxypropionaldehyde is 2:1-20:1.

3. The method according to claim 1, wherein a chemical formula of the precious metal-supported eggshell catalyst is M-X/A, wherein A is the carrier, M is a precious metal element and X is a combination of any one or more than two of the precious metal element, the alkaline earth metal element, the transition metal element, and the lanthanide series metal element.

4. The method according to claim 1, wherein the precious metal element of the active component comprises a combination of any one or more than two of Pt, Pd, Ir, and Ru; and/or the promoter comprises a combination of any one or more than two of Ca, La, Rh, Pt, Pd, Ir and Ru and/or a metal oxide of Ca, Ni, Co, Mn, Cu, La and Rh.

5. The method according to claim 1, wherein a support amount of the precious metal of the active component in the precious metal-supported eggshell catalyst is 0.1-10 wt % whether as a main catalyst or as a promoter; and/or a support amount of a non-noble metal promoter in the precious metal-supported eggshell catalyst is 1-50 wt %; and/or in the precious metal-supported eggshell catalyst, based on a metal element, a mass ratio of the promoter to the precious metal is 2:1-500:1.

6. The method according to claim 1, wherein the carrier is a particle in a shape of a Raschig ring, a material of the carrier comprises an oxide and/or a molecular sieve; the oxide comprises a combination of any one or more than two of γ-$Al_2O_3$, $SiO_2$, MgO, $TiO_2$, $ZrO_2$ and an amorphous aluminum silicate; the molecular sieve comprises a combination of any one or more than two of ZSM-5, an H~ molecular sieve, MCM-49, MCM-22, SAPO-11, SAPO-34, mordenite, β Zeolite, L zeolite, Y zeolite and ultra-stable Y zeolite;

and/or, a particle size of the carrier is 1-8 mm.

7. The preparation method according to claim 2, wherein a chemical formula of the precious metal-supported eggshell catalyst is M-X/A, wherein A is the carrier, M is a precious metal element and X is a combination of any one or more than two of the precious metal element, the alkaline earth metal element, the transition metal element, and the lanthanide series metal element.

8. The preparation method according to claim 2, wherein the precious metal element the active component comprises a combination of any one or more than two of Pt, Pd, Ir, and Ru; and/or the promoter comprises a combination of any one or more than two of Ca, Ni, Co, Mn, Cu, La, Rh, Pt, Pd, Ir, and Ru and/or a metal oxide of Ca, Ni, Co, Mn, Cu, La and Rh.

* * * * *